United States Patent
Gao et al.

(10) Patent No.: US 12,059,250 B2
(45) Date of Patent: Aug. 13, 2024

(54) SYSTEMS AND METHODS FOR POWERING AUTONOMOUS SWEAT SENSOR

(71) Applicant: California Institute of Technology, Pasadena, CA (US)

(72) Inventors: Wei Gao, Pasadena, CA (US); Yu Song, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 214 days.

(21) Appl. No.: 17/486,724

(22) Filed: Sep. 27, 2021

(65) Prior Publication Data

US 2022/0110555 A1 Apr. 14, 2022

Related U.S. Application Data

(60) Provisional application No. 63/091,366, filed on Oct. 14, 2020.

(51) Int. Cl.
| | |
|---|---|
| *A61B 5/145* | (2006.01) |
| *A61B 5/00* | (2006.01) |
| *H02N 1/04* | (2006.01) |

(52) U.S. Cl.
CPC .......... *A61B 5/14517* (2013.01); *A61B 5/002* (2013.01); *A61B 5/6823* (2013.01);
(Continued)

(58) Field of Classification Search
CPC ... A61B 5/14517; A61B 5/002; A61B 5/6823; A61B 5/6824; A61B 5/6833;
(Continued)

(56) References Cited

U.S. PATENT DOCUMENTS

| | | | |
|---|---|---|---|
| 2014/0246951 A1* | 9/2014 | Wang | H02N 1/04 310/310 |
| 2016/0149518 A1* | 5/2016 | Wang | F03B 13/14 310/310 |

(Continued)

FOREIGN PATENT DOCUMENTS

| | | | |
|---|---|---|---|
| KR | 20160105176 | * | 9/2016 |
| WO | WO 2017108546 | * | 6/2017 |
| WO | WO 2018223090 | * | 12/2018 |

OTHER PUBLICATIONS

Self-powered flexible printed circuit board with integrated triboelectric generator; Bo Meng et al. (Year: 2013).*

*Primary Examiner* — Ahmed Elnakib
(74) *Attorney, Agent, or Firm* — Sheppard Mullin Richter & Hampton LLP

(57) ABSTRACT

Systems and methods for a self-powered wireless wearable sensor system include a freestanding triboelectric nanogenerator (FTENG), used as a power source for a wearable sensor. The FTENG includes stator panels and corresponding slider panels with a grating pattern. Movement, such as cardiovascular exercise causes the slider panel(s) to slide across the stator panel(s) inducing a charge and powering a wearable device sufficiently to support data transmission and continuous monitoring. An integrated self-powered wireless wearable sensor system includes a microfluidic sweat sensor patch which may be connected to lower-power wireless sensor circuitry for regulating power efficiently and is powered by the FTENG.

13 Claims, 8 Drawing Sheets

(52) U.S. Cl.
CPC .......... *A61B 5/6824* (2013.01); *A61B 5/6833* (2013.01); *H02N 1/04* (2013.01); *A61B 2560/0214* (2013.01); *A61B 2562/046* (2013.01); *A61B 2562/166* (2013.01)

(58) Field of Classification Search
CPC ...... A61B 2560/0214; A61B 2562/046; A61B 2562/166; A61B 5/6832; H02N 1/04
USPC .......................................... 310/20, 309, 310
See application file for complete search history.

(56) References Cited

U.S. PATENT DOCUMENTS

| | | | |
|---|---|---|---|
| 2016/0365808 A1* | 12/2016 | Kim | H02N 1/04 |
| 2017/0331396 A1* | 11/2017 | Byun | H02N 1/04 |
| 2018/0070870 A1* | 3/2018 | Emaminejad | A61B 5/4266 |
| 2018/0146545 A1* | 5/2018 | Wang | H05K 1/095 |
| 2018/0294745 A1* | 10/2018 | Park | C08L 53/00 |
| 2020/0316366 A1* | 10/2020 | Wang | A61F 13/0273 |
| 2021/0208121 A1* | 7/2021 | Su | G01N 33/0031 |
| 2021/0226558 A1* | 7/2021 | Lin | H02N 1/08 |
| 2022/0110555 A1* | 4/2022 | Gao | A61B 5/6832 |
| 2023/0181096 A1* | 6/2023 | Gao | H02S 40/30 |
| | | | 600/301 |

* cited by examiner

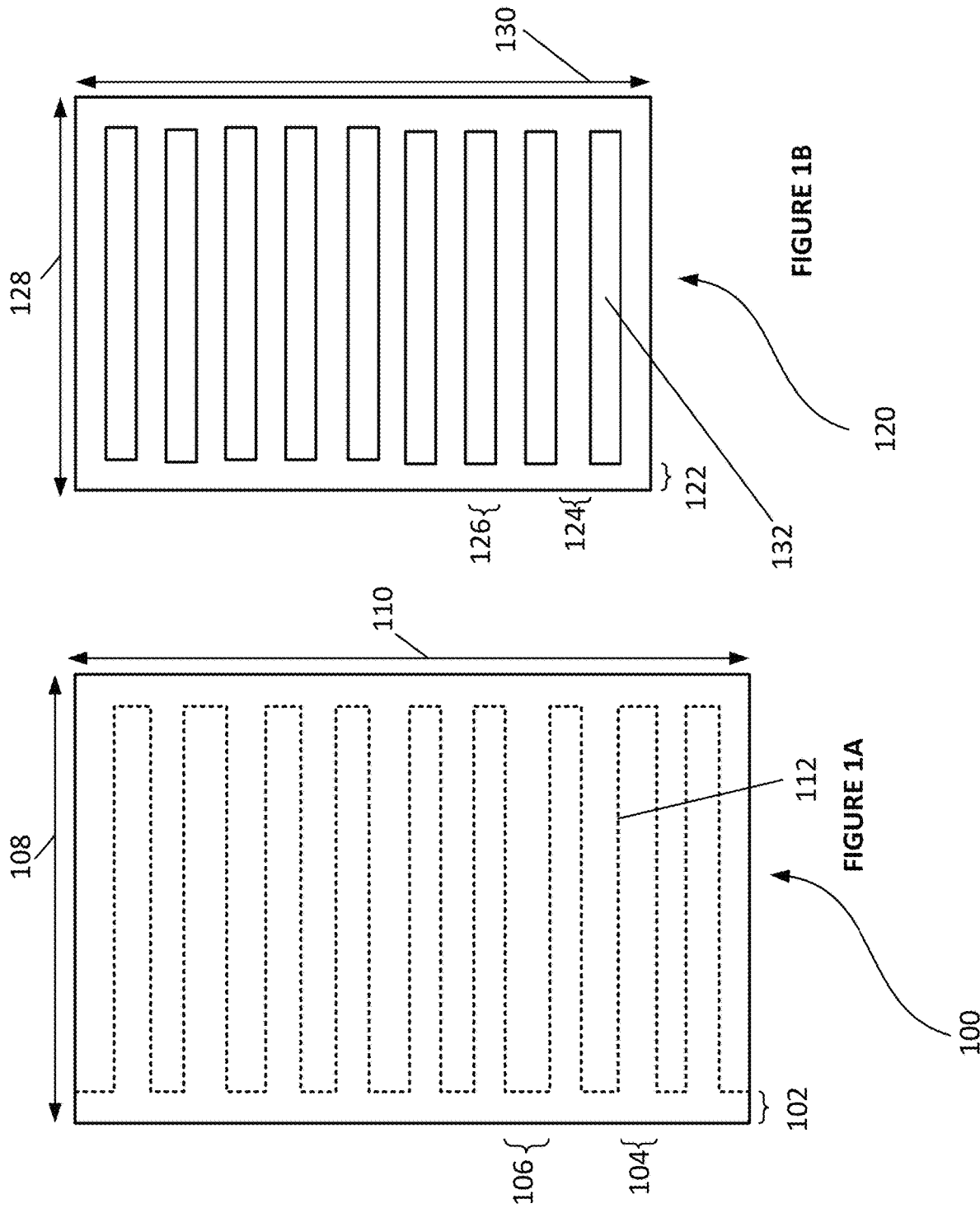

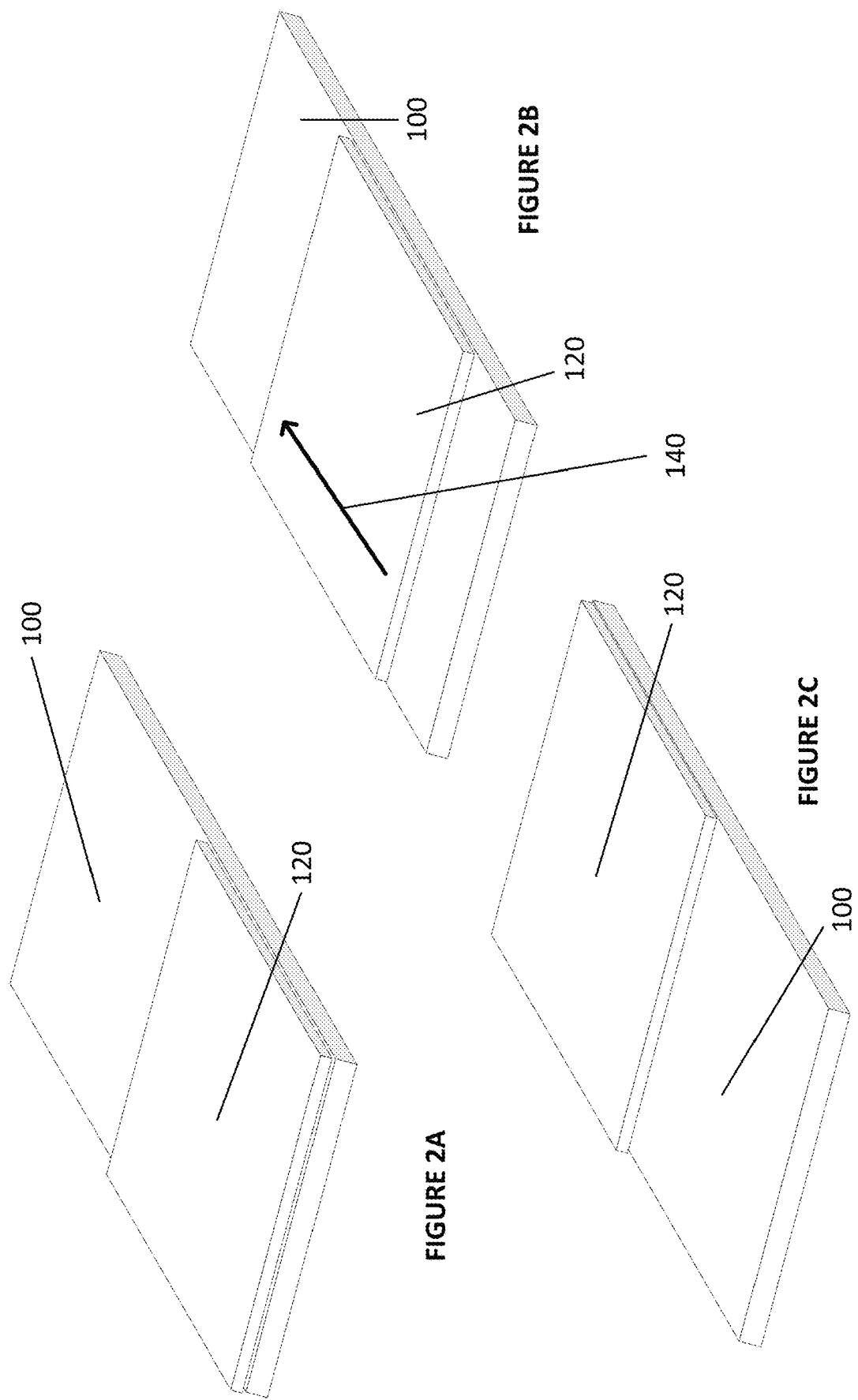

SYSTEMS AND METHODS FOR POWERING AUTONOMOUS SWEAT SENSOR

CROSS-REFERENCE TO RELATED APPLICATIONS

This application claims the benefit of U.S. Provisional Application No. 63/091,366 filed Oct. 14, 2020, which is hereby incorporated herein by reference in its entirety.

TECHNICAL FIELD

The present disclosure relates generally to systems and methods for powering a wearable device. In particular, some implementations may relate to methods for powering a wearable device using a kinetic power source, such that the device may function autonomously.

BACKGROUND

Wearable bioelectronic technology offers many advantages for personalized health monitoring. Wearable devices are non-invasive and present less user error than other monitoring methods. Additionally, wearable devices offer the potential to monitor health status over time as opposed to collecting a sample that reflects health status at only a snap shot in time. This type of real-time monitoring offers more accurate and individualized diagnosis, treatment, and prevention for health conditions. Specifically wearable devices can measure pulse, respiration rate, temperature and other health status indicators.

Sweat sensors are one type of wearable bioelectronic sensors that are particularly desirable because sweat contains many key biomarkers including electrolytes, metabolites, amino acids, hormones, and drug levels. However, existing sweat sensors face several key problems. These sensors often require a large sample of sweat to provide accurate analysis of biomarkers. This requires a large and more powerful device which may not be suitable as a wearable. Additionally, existing sweat sensors have high power demands. Therefore, monitoring and especially continuous monitoring presents a challenge. Existing models are limited in the amount of time they can operate continuously due to their power consumption and limits on power storage. Existing models present additional challenges including that they require complex fabrication and are difficult to reproduce in large quantities in an affordable way. They are also fragile and not suitable as wearable devices for long periods. They also suffer from low power density. Because wearable devices practically must be small and light-weight, high power density is an important characteristic of an efficient and effective wearable device.

Because of the high power demands required, currently existing wearable health monitoring systems are typically powered by batteries. Many types of batteries add weight and bulk to the device. Some also pose the risk of burns. Even lightweight batteries have significant drawbacks including that they need to be charged and replaced frequently.

SUMMARY

Systems and methods are described herein for a self-powered wireless biosensor system. Such autonomous methods offer advantages over batteries. Autonomous powering methods include powering from human motion, and powering from biofluids. However, generally available autonomous powering methods may not be sufficient to meet the efficiency and power demands for powering a wearable biosensor device.

One type of autonomous power method may use triboelectric nanogenerators (TENGs). These devices use inductive and triboelectric effects to convert mechanical energy created by motion into electric energy capable of powering an electric device. Therefore, operation of devices powered with TENGs is independent from external energy sources such as batteries, which might run out, or the sun which may be unavailable or obscured. However, TENGs may suffer from low power density, inefficient power management, and a lack of power continuity and longevity. Accordingly, TENG power sources have been unable to meet the power demands of a continuously monitoring wearable biosensor.

Embodiments of the present disclosure provide a kinematic power system for a wearable device. The system may include a stator. The stator may have two or more interdigital electrode arrays. A kinematic power system for a wearable device may also include a slider having a grating pattern. The slider may be slidably coupled to the stator, enabling the slider to move across the stator. The slider may be configured to enable planar movement between a first position relative to the stator and a second position relative to the stator. A kinematic power system for a wearable device may also include a plurality of triboelectric materials. The triboelectric materials may coat the slider and/or the stator. For example, the stator may be coated with a material having triboelectric properties such as polytetrafluoroethylene (PTFE). For example, the slider may be coated with a material having triboelectric properties such as copper. The two materials, for example PTFE and copper, may form a desirable triboelectric pair and may together be conducive to inducing a charge when the slider moves across the stator.

In a kinematic power system for a wearable device including a slider and stator, the dimensions of the slider and stator may be carefully selected to ensure sufficient power is achieved to power the wearable device and/or to enable the wearable device to perform continuous monitoring over a period of time. Sufficient power may also enable the wearable device to transmit data to a user interface or another source where the data can be viewed and analyzed. For example, the inter-electrode distance for the stator may be between about two and eighteen millimeters. About in this instance means plus or minus 2 millimeters. For example, the slider grating pattern may include a plurality of apertures. Each aperture may have a width dimension between about 1 and 3 millimeters. About in this instance means plus or minus 0.2 millimeters. Additionally, slider-stator systems may include different numbers of sliders and stators optimal powering. For example, one embodiment may include a single stator and a single slider. Another embodiment may include three stators connected in a three-panel arrangement, and three sliders, also connected in a three-panel arrangement. Another embodiment may include six stator panels in a three-panel arrangement, which may be used with a three-panel slider. Other numbers of stator and/or slider panels are also possible.

To ensure a kinematic power system for a wearable device is compatible with wearable devices and/or related circuitry, and that the power system can withstand long term use without compromising its ability to supply needed power, a stator may be fabricated using flexible printed circuit board technology (FPCB). Fabricating a stator using FPCB may enable application to the human body with comprising components as they contour to stay attached. Fabricating a stator using FPCB may also ensure compatibility with various sensors, circuitry, and other elements also fabricated using FPCB such that the power system may be integrated into a wearable platform or system.

A self-powered wearable system may include a freestanding triboelectric nanogenerator (FTENG), a low-power wireless sensor circuitry, and a wearable sensor patch. To ensure compatibility of these elements and/or for application to the human body without comprising the components or effectiveness of the system, the FTENG, circuitry, and patch may all be fabricated using FPCB and may all be supported by a single FPCB platform.

The FTENG may include one or more interdigital stator panels and one or more grating patterned slider panels, as describe in the preceding paragraphs. The FTENG may power the wearable system. The slider may move from a first position relative to the stator to a second position relative to the stator, inducing a charge when a human subject wearing the wearable device engages in certain types of cardiovascular exercise. This enables the system to be powered even when other power sources, such as battery power, conventional electrical power provided via an outlet, or the sun, are not available.

The wearable sensor patch of the system may be a microfluidic sweat sensor patch. Sweat may contain many indications of health including ion concentrations, amino acid levels, hormone levels, vitamin and mineral levels, presence of drugs, and other indicators of health. A microfluidic sweat sensor may collect a sweat sample from a sweat gland in a reservoir. The sample may be periodically refreshed. The microfluidic sweat sensor patch may allow for continuous monitoring of health indicators over a period of time. As the sweat samples refresh, the new samples may reveals changes or trends in the body. A sweat sample may operate using a small amount of sweat and may not have significant power needs compared with other types of biosensors. A sweat sensor may also be non-invasive so that a human subject may be comfortable wearing a sweat sensor patch over a period of time. A sweat sensor patch may also be fabricated inexpensively and may disposable such that a human subject may periodically replace a sweat sample patch as needed.

A self-powered wearable system may also include a user interface. A user interface may be available on a mobile device, for instance via an application. A user may access data collected form a wearable biosensor via the user interface. Data collected form a wearable biosensor may be transmitted such that it can be accessed via the user interface using a wireless method, such as Bluetooth. The FTENG may supply sufficient power for a Bluetooth transmission or another type of wireless transmission of data.

A self-powered wearable system may also include low-power wireless sensor circuitry which may include modules and elements for efficient power management. Efficient power management ensures meeting the high power needs associated with wearable devices as well as meeting power needs for continuous monitoring over a period of time. Low-power wireless sensor circuitry may include a power management integrated circuit (PMIC) for power management. The PMIC may include two capacitors in parallel. The PMIC may allow a flow of charge when capacitors are fully charged and may disconnect capacitors when they fall below a certain power threshold. This may ensure that the system receives stable voltage over a period of time. Low-power wireless sensor circuitry may also include a Bluetooth low energy programmed system on a chip (BLE PSoC) module. The BLE PSoC may enable Bluetooth data transmission without incurring steep energy costs.

The FTENG and low-power wireless sensor circuitry supported by the FPCB platform may be configured to power and support different type of wearable sensor patches. For instance, identical disposable sweat sensor patches may be replaced without compromising the system effectiveness. Alternatively, sweat sensor patches having different functions, e.g., one that measure hormone levels and one that measures amino acid levels, may both be compatible with the system. Alternatively, a different type of biosensor altogether, such as a body temperature sensor, may be connected to the system.

A self-powered wearable system, as described in the preceding paragraphs, may be configured to supply stable voltage for a period up to and exceeding four hours.

A method for powering a wearable device may comprise wearing the wearable device. The wearable device may include a stator panel. The stator panel may have two or more interdigital electrode arrays. The wearable device may also include a slider panel. The slider panel may have a grating pattern. The slider may slidably couple to the stator, enabling movement between a first position relative to the stator and a second position relative to the stator. The slider may be slidably coupled to the stator such that the slider and stator are connected through electrostatic charge. In other words, the a charge is produced when the slider and stator come into contact with each other. The contact may not be direct physical contact. The contact may be a threshold proximity. For example, a charge may be induced when the slider and stator come within about five centimeters of each other. The slider may be slidably coupled to the stator enabling planar movement between a first position relative to the stator and a second position relative to the stator. Alternatively, the slider may be slidably coupled to the stator enabling some other type of movement, for example curvilinear movement, between a first position relative to the stator and a second position relative to the stator.

A method for powering a wearable device may also comprise moving. The movement may cause the slider to move between the first position and second position relative to the stator. Wearing the wearable device may further involve applying the stator panel to a human torso and applying the slider panel to the insider of a human arm. Moving comprise a certain type of cardiovascular exercise that causes the inside of the human arm to slide against the human torso. This type of exercise may be jogging, running, rowing, training on an elliptical, or another type of exercise that produces that desired sliding effect. It may also be possible to attach the stator and slider to other parts of the human body that slide against each other during certain types of cardiovascular exercise. Moving may comprise sustain movement for a period up to and including two hours. The method may also include a further step of accessing sample data collected by a wearable device using a user interface.

Other features and aspects of the disclosure will become apparent from the following detailed description, taken in conjunction with the accompanying drawings, which illustrate, by way of example, the features in accordance with various embodiments. The summary is not intended to limit the scope of the invention, which is defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 1A is a diagram showing an example of a stator for use in a self-powered wearable device.

FIG. 1B is a diagram showing an example of a slider for use in a self-powered wearable device.

FIG. 2A is a diagram showing an example of a stator and slider for use in a self-powered device showing the slider occupying a first position relative to the stator.

FIG. 2B is a diagram showing an example of a stator and slider for use in a self-powered device showing the slider as it moves from a first position to a second position.

FIG. 2C is a diagram showing an example of a stator and slider for use in a self-powered device showing the slider occupying a second position relative to the stator.

FIG. 6 is a flow diagram showing a method for powering an autonomous wearable device.

Figure 3A:
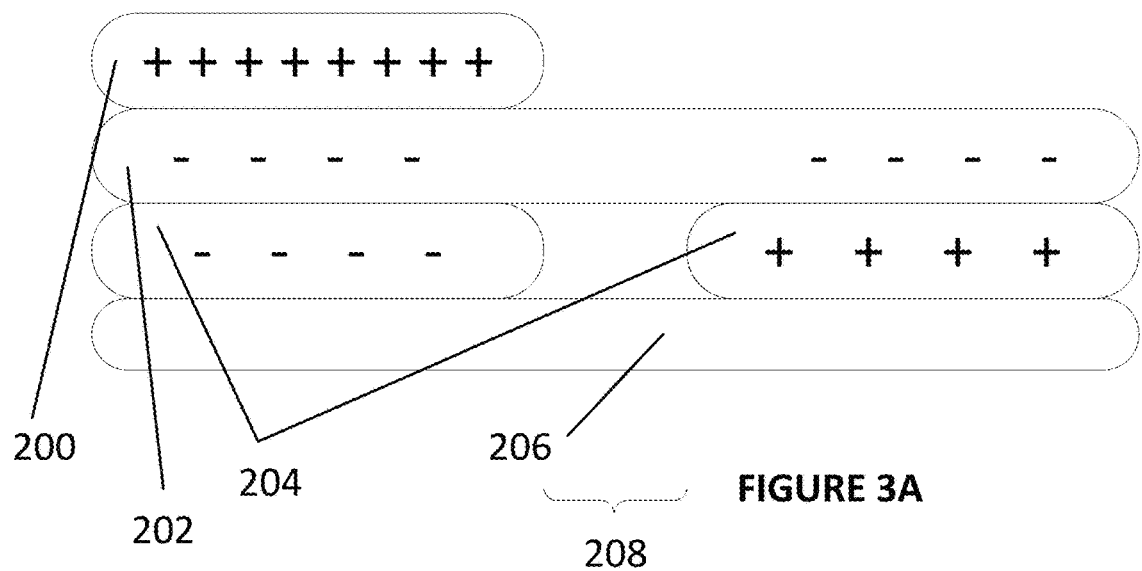
FIG. 3A is a diagram showing an example of a stator and slider for use in a self-powered device showing the slider occupying a first position relative to the stator.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION

Wearable devices may offer highly desirable, non-invasive, and continuous monitoring of key health indicators. However, these devices are difficult to design since health monitoring and especially continuous monitoring can have high energy demands. One type of desirable wearable is a sweat sensor. A carefully designed and efficiently designed system may enable autonomous powering of a sweat sensor. Several types of autonomous powering are available including power by human motion.

The embodiments described herein relate to a battery-free, fully self-powered wearable bioelectric medical monitoring system. The system may include an autonomous power source, a low-power wireless sensor circuitry, and a sensor patch, all supported by a single, flexible printed circuit board. In an embodiment, the sensor patch may be a microfluidic sweat sensor. In an embodiment, the autonomous power source may be a freestanding mode triboelectric nanogenerator (FTENG). A fully integrated battery free triboelectrically-driven system for multiplexed sweat sensing is described in the following paragraphs. This is an example of the type of integrated system that may solve industry issues regarding self-powering of a wearable biosensor system. Other types of systems are also possible and this example is not intended to be limiting.

FTENG

An FTENG for use in powering a wearable biosensor system may include a stator and a slider. The FTENG makes use of tribo-pairs to obtain a strong electrification effect when the slider slides across the surface of the stator. These pairs may be copper and polytetrafluoroethylene (PTFE). The stator and the slider may be coated with these materials or with other materials demonstrating desirable triboelectric properties. The FTENG may be fabricated with flexible printed circuit board (FPCB) technology. FPCB fabrication ensures the FTENG will not be compromised even when applied to the human body as part of a wearable system. It also ensures the FTENG will be compatible with other system components including circuitry and one or more wearable biosensor devices.

FIG. 1A is a diagram showing an example of a stator 100. The stator includes electrodes 112 forming an interdigital structure. The stator also includes an inter-electrode 208 distance which is optimized for efficient power generation. The stator includes other dimensional parameters such as height 102, gap 104, offset 106, width 108, and length 110.

FIG. 1B is a diagram showing an example of a slider 120. The slider includes a grating pattern comprising several open grates 132. The slider also includes dimensional parameters such as height 122, grate width 126, distance between grates 124, width 128, and length 130. When the slider 100 is placed on top of the stator 120, the grating pattern of the slider 100 and the interdigital structure of the stator 120 are periodically complimentary.

As shown in FIGS. 2A, 2B, and 2C, the slider 120 is slidably coupled to the stator 100, enabling movement between a first and second position relative to the stator 100. In the first position, shown in FIG. 2A, the grating pattern 132 of the slider 120 fully overlaps with a stator electrode 112. Therefore, the system is in electrostatic equilibrium and no charge flows through the electrode 112. As shown in FIG. 2B, the slider 120 may slide relative to the stator 100 in a sliding direction 140. As the slider 120 slides across the stator 100, charge flows between the stator electrode(s) 112 until the slider 120 arrives in the second position relative to the stator 100. FIG. 2C shows the slider 120 occupying the second position relative to the stator 100. In this position, the grating pattern 132 of the slider 120 fully overlaps with the second electrode 112 of the stator 100. The second electrode 112 of the stator 100 may have reversed polarity.

Figure 3B:
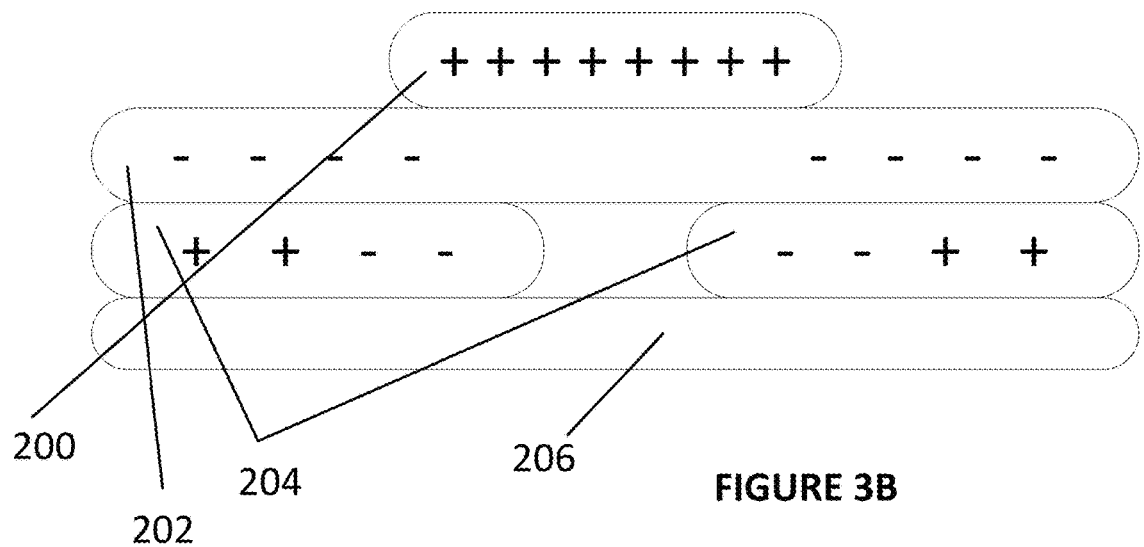
FIG. 3B is a diagram showing an example of a stator and slider for use in a self-powered device showing the slider as it moves from a first position to a second position.
Figure 3C:
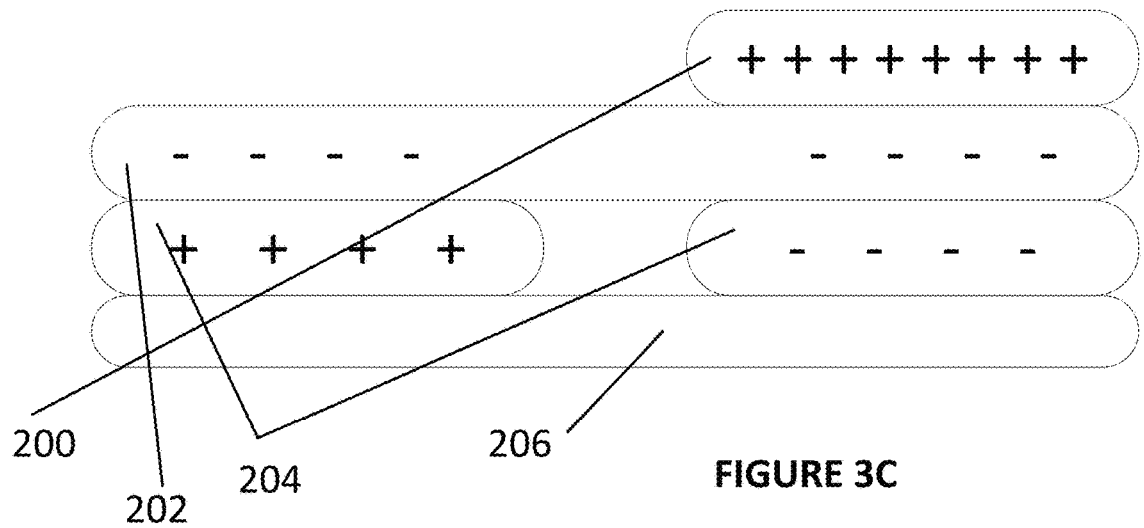
FIG. 3C is a diagram showing an example of a stator and slider for use in a self-powered device showing the slider occupying a second position relative to the stator.

FIG. 3 shows examples of the slider and stator in the same positions as shown in FIG. 2 from a front perspective. FIG. 3 also shows the triboelectric material coating the stator 100 and slider 120. For example, FIGS. 3A, 3B, and 3C show a copper coating 200 on the slider. The copper coating has a strong positive charge. FIGS. 3A, 3B, and 3C also show a PTFE coating 202 on the stator 120. The PTFE coating is less positively charged than the copper coating. FIGS. 3A, 3B, and 3C also show an electroless nickel/immersion gold (ENIG) surface finish 204 on the electrode area 112 of the stator 120 and a polyimide base 206. The polyimide material is durable which allows the FTENG to be integrated into a wearable system appropriate for continuous monitoring of the human body over periods of time without degradation of the components.

Contact electrification occurs when certain materials become electrically charged after they have contact with a different material and then are separated from that other material. This is known in the art as the triboelectric effect. Different materials have different triboelectric properties. Copper, for instance, is more triboelectrically positive than other materials, such as polytetrafluoroethylene (PTFE). Therefore, when copper comes into contact with PTFE, electrons will be repelled from the copper and will accumulate on the PTFE. The PTFE is an attractive choice because, as empirically determined, it resists scratching and degrading over time.

In embodiments, the FTENG may operate at varying frequencies. These frequencies correspond to maximum currents. Examples frequencies and currents are included in Table 1:

| Frequency (Hz) | 0.5 | 1.25 | 3.3 |
|---|---|---|---|
| Current (μA) | 8.39 | 19.11 | 42.25 |

With a load resistance of 4.7 MΩ and actuation frequency of 1.5 Hz, the FTENG can achieve a maximum power output of 0.94 mW.

Figure 4A:
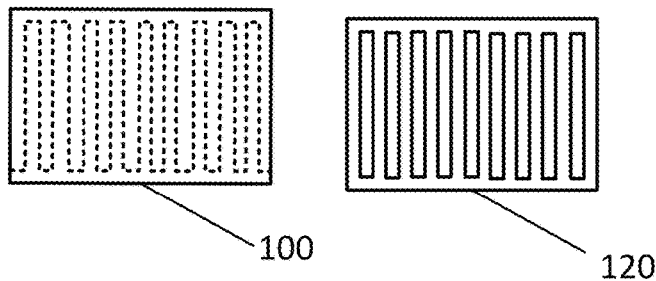
FIG. 4A is a diagram of an example of stator and slider in a one-panel configuration.
Figure 4B:
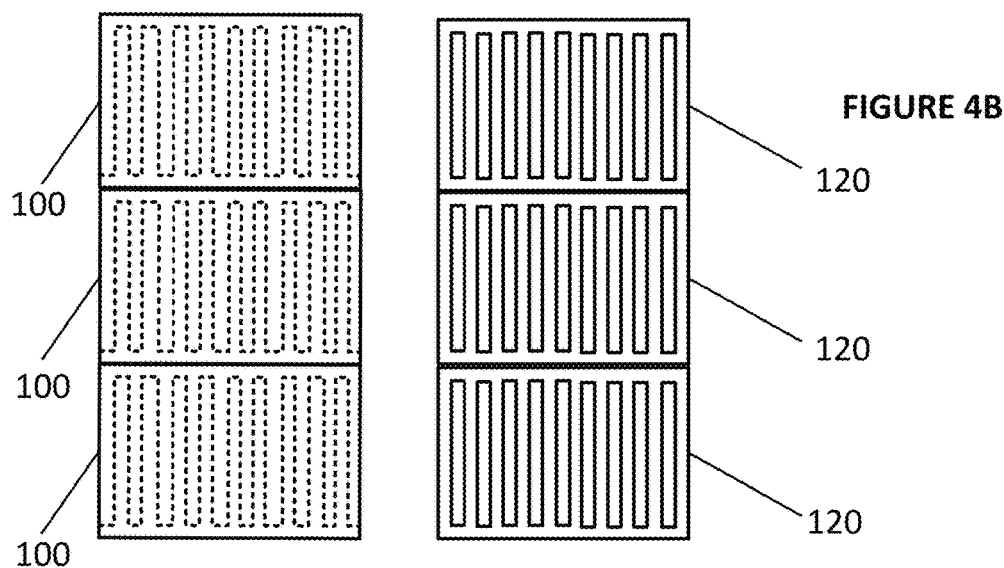
FIG. 4B is a diagram of an example of stator and slider in a three-panel configuration.
Figure 4C:
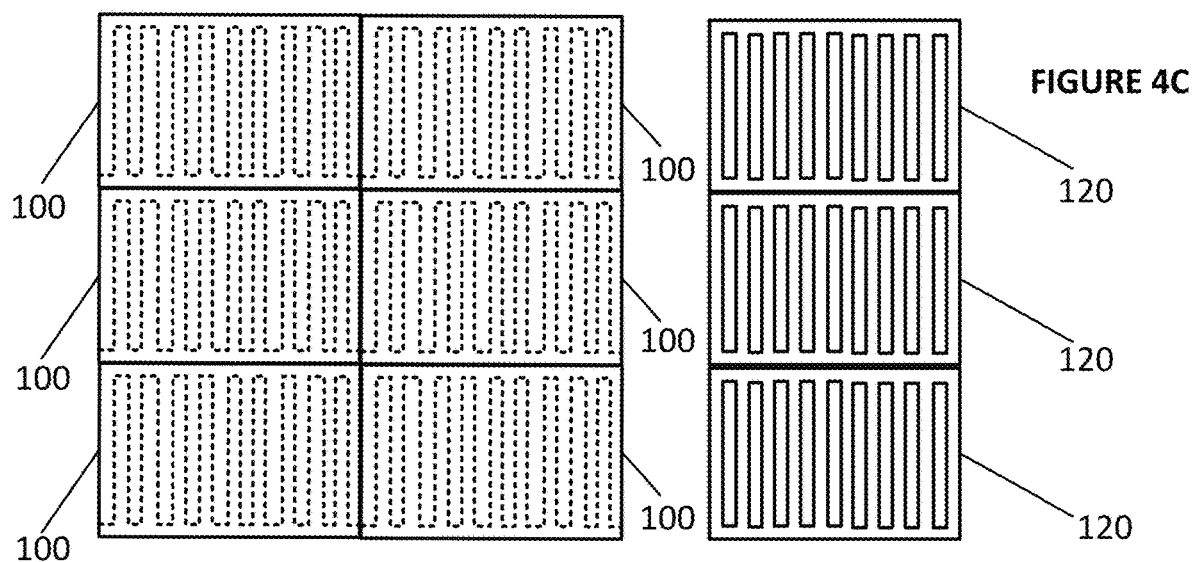
FIG. 4C is a diagram of an example of stator and slider in a six-panel configuration.

FTENGs having 1-panel, 3-panel, and 6-panel configurations may be used to power wearable devices. FIGS. 4A, 4B, and 4C show these configurations. For example, in an embodiment, a 3-panel FTENG actuated at a working frequency of 1.5 Hz may repeatedly charge a 47 μF capacitor over a two hour period from 0 to 2 V. A plurality of FTENGs may be connected in parallel to achieve increased power output.

Sweat Sensor Patch

A sweat sensor patch may include a biosensor array for sweat analyte analysis. The analysis may be based on ion-selective electrodes. The sweat sensor patch may include laser engraved microfluidic channels. The electrodes may have different coatings including polyvinyl butyral (PVB) to maintain a steady potential to measure electrolytes in the sweat. The sweat sensor may also measure pH and salt concentration. The sensor may measure other ion concentrations. The sensor may be configured to make other health measurements including amino acid levels, hormone levels, and drug levels.

The sweat sensor patch may be fabricated with laser patterned microfluidic lasers and may be easily reproduced. The sensor is also flexible which allows for attachment to the human body without comprising the structure of the sensor. The sensor patch may be attached to the human body with medical adhesive. The sweat sensor may make continuous biologic measurements over a period of time. It may detect changes in the human body and reflect updated measurements within minutes of the change.

Figures 5A, 5B:
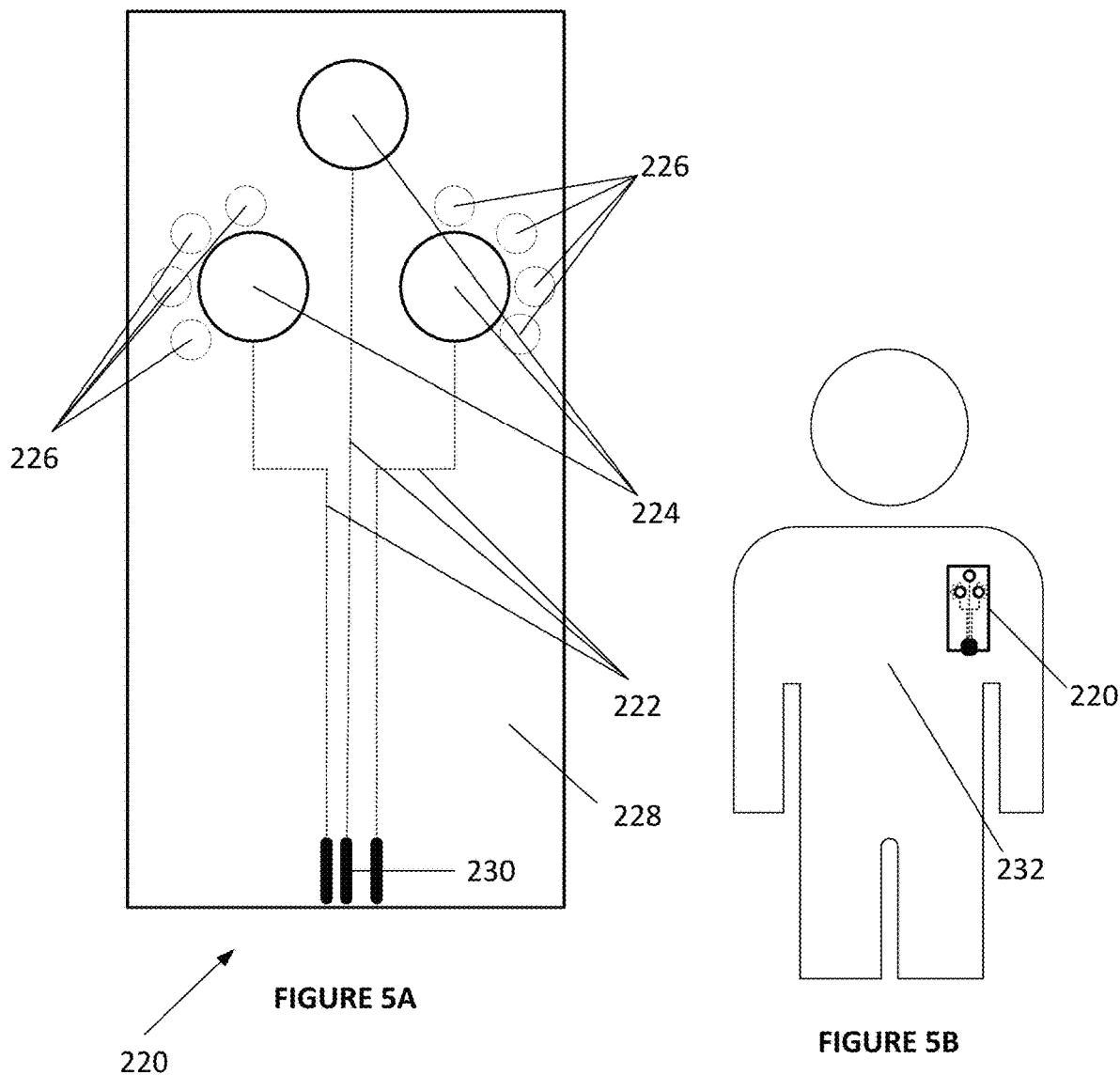
FIG. 5A is a diagram showing an example of a microfluidic sweat sensor patch.
FIG. 5B is a diagram showing an example of a microfluidic sweat sensor patch applied to a human body.

FIG. 5A shows an example of a sweat sensor patch 220. The sweat sensor patch includes laser engraved microfluidic channels 222. It also includes reservoirs 224 to collect and analyze sweat samples. The reservoirs 224 may be placed near several neighboring sweat glands 226 which may be induced to produce samples. The sweat sensor patch may be applied to human skin using a medical tape layer 228. For example, laser patterned microfluidic layers containing laser engraved microfluidic channels 222 may be attached to a polyethylene terephthalate (PET) sensor substrate in a layered structure so that the microfluidic chip layer lies between two layers of medical tape 228. This configuration prevents leakage and secures the sensor to the human body. The sweat sensor patch 220 also includes a circuitry connection point 230 for integration into a self-powered sweat sensor system.

FIG. 5B shows an example of a sweat sensor patch 220 applied to a human body 232. The sweat sensor may be applied to several areas on the human body. In one embodiment, the sweat sensor may be applied to the human torso. The sweat sensor patch may be easily affixed to the human body using medical tape or medical adhesive. The sweat sensor patch may be easily removed from the human body by peeling off the sweat sensor. New sweat sensors may be attached to the body on a periodic basis. For example, a human subject may replace the sweat sensor patch daily. New sweat sensor patches may integrate with other existing components of a self-powered sweat sensor system. For example, a new patch may connect to existing circuitry which may connect to a means to power the sweat sensor system.

System Integration

The FTENG-powered wearable sweat sensor system may include several components. It may include an interdigital stator. It may also include a power-management integrated circuit (PMIC). It may also include a low dropout (LDO) voltage regulator, two low power instrumentation amplifiers, and a Bluetooth low energy (BLE) programmed system on a chip (PSoC) module. All of these components may be seamlessly integrated onto a polyimide based flexible printed circuit board (FPCB). The system may further include a grating patterned FTENG slider and a microfluidic sensor patch.

Design of the FTENG and electronic circuitry on a single printed circuit board allows for seamlessly interchanging the sensor patch and/or integrating other types of sensors that are suitable for similar self-powering mechanisms. The integration of the entire system on a FPCB allows for easy application onto the human body without comprising the effectiveness of the system. It also allows the sweat sensor patch, which may be more cost effective to fabricate as a disposable device to be replaced frequently while the other components, which may be more cost effective to manufacture as permanent devices, do not need to be replaced.

Because continuous monitoring has high power needs, efficiency is critical to an effective design. A PMIC may be included in the system to manage power generated by the FTENG so that it efficiently powers the device while minimizing energy waste. The PMIC can store energy generated by the FTENG in two parallel capacitors. Then, stored power can be released only when needed using a switch control logic system. Capacitors can be disconnected and reconnected on an alternating basis only when fully charged.

A system can also conserve energy by reducing power needs. Continuous monitoring requires a lot of energy and even more energy is required when data is transmitted wirelessly on a continuous basis, as disclosed herein. Therefore, a system may include a Bluetooth low energy programmed system on a chip (BLE PSoC) module to maintain data transmission via Bluetooth without incurring steep energy costs.

Figure 6:
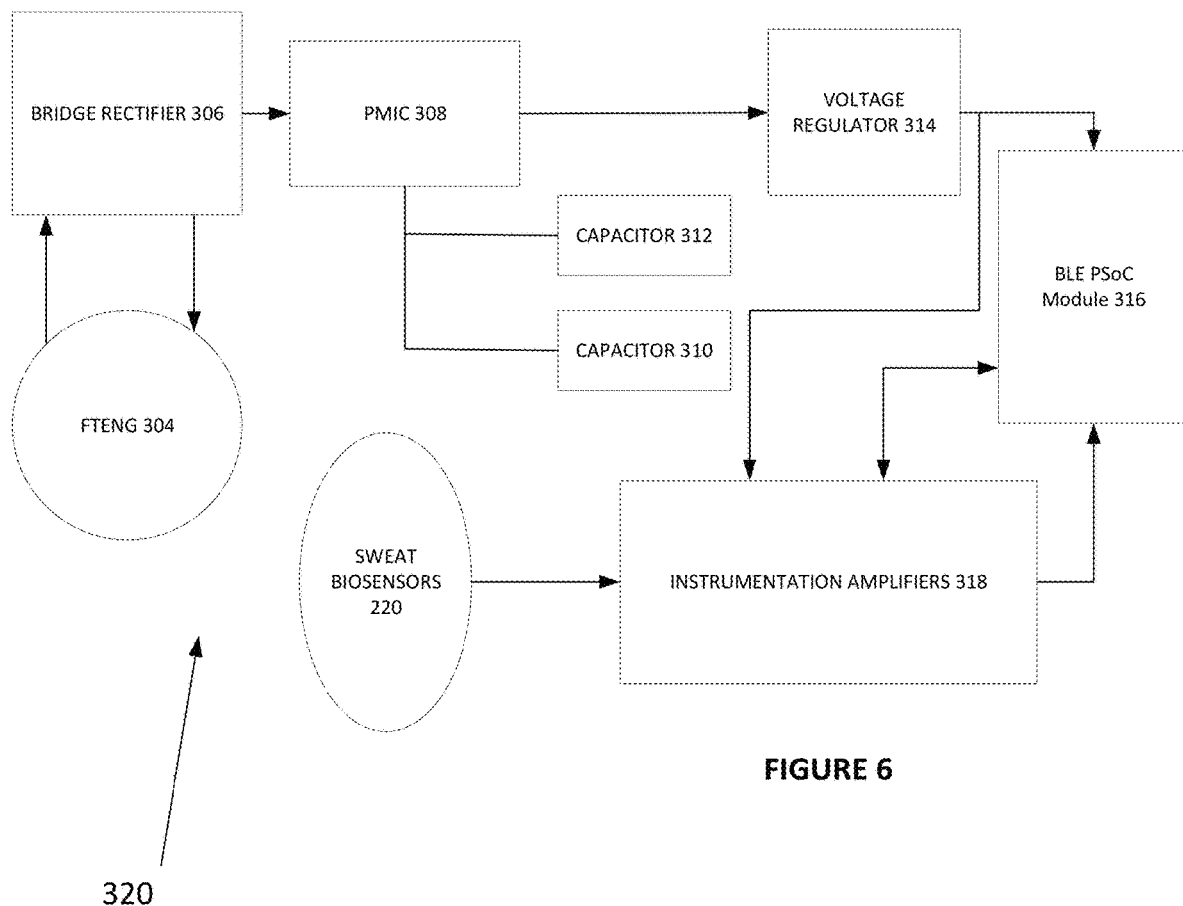
FIG. 6 is a diagram showing an example of a low-power wireless sensor circuitry for managing power supplied by an FTENG to power a biosensor device.

FIG. 6 shows an example of the electronic circuitry for the self-powered wireless biosensor. The FTENG 304 may power the system. The FTENG may include an interdigital stator. It may also include a grating slider. When a person wearing the self-powered wireless biosensor moves, the movement may cause the slider to slide across the stator. This may generate a charge, converting the mechanical energy of the movement into electric energy. Power from the FTENG may travel through a bridge rectifier 306. The bridge rectifier 306 may assist in converting high voltage AC signals generated by the FTENG into a DC signal. The signal may then travel to the PMIC 308. The PMIC 308 may manage energy generated by the FTENG to minimize power waste. The PMIC 308 may accomplish this efficient power management by storing the FTENG generated energy in two capacitors 310, 312 in parallel. Resistors are programmed such that stored power is only released when certain thresholds are achieved. When the voltage of the capacitors 310, 312 storing the energy reach a threshold voltage, the capacitors 310, 312 supply energy until their voltages reach a lower threshold. Then, the PMIC 308 disconnects the capacitors 310, 312 until they are charged back up to the upper threshold. The energy passing from the capacitors 310, 312 is then regulated by a voltage regulator 314 which provides the rest of the circuitry with a stable voltage.

When the capacitors are charged, energy passes through the voltage regulator to the BLE PSoC Module 316 which then initiates an operation cycle. This enables data captured by the sweat biosensors 220 to be transmitted via Bluetooth. During its operating cycle, the PSoC Module 316 makes use of instrumentation amplifiers 318 to collect and analyze biologic samples. The instrumentation amplifiers 318 are such down after a measurement cycle completes to conserve power. This configuration may supply power to the FPCB for a period of over four hours.

Self-Powered Wearable Biosensor System on Human Body

The system can be attached directly to human skin. This configuration allows for efficient powering of skin-interfacing wearables. Waterproof medical tape may be used to secure the device to human skin. The device may be secured to the human torso or another suitable place on the human body.

Certain types of exercise and/or movement of the human body produce a sliding motion between the torso and the inner arm. These exercises may include, for example, running, jogging, rowing, training on an elliptical or other cardiovascular exercise type equipment, and other types of exercise. This type of movement may power the FTENG. The stator of the FTENG may be attached to the human torso. The slider of the FTENG may be attached to the inner arm such that when the human body moves, the slider slides against the stator. This sliding motion transforms the mechanical energy of the body movement into electrical energy as charge accumulates.

Figure 7B:
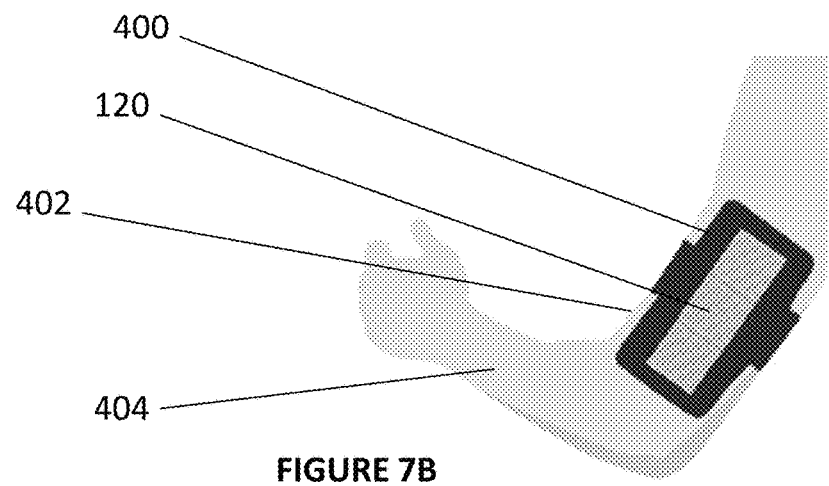
FIG. 7B is a diagram showing an example of a slider panel worn by a human being.
Figure 7A:
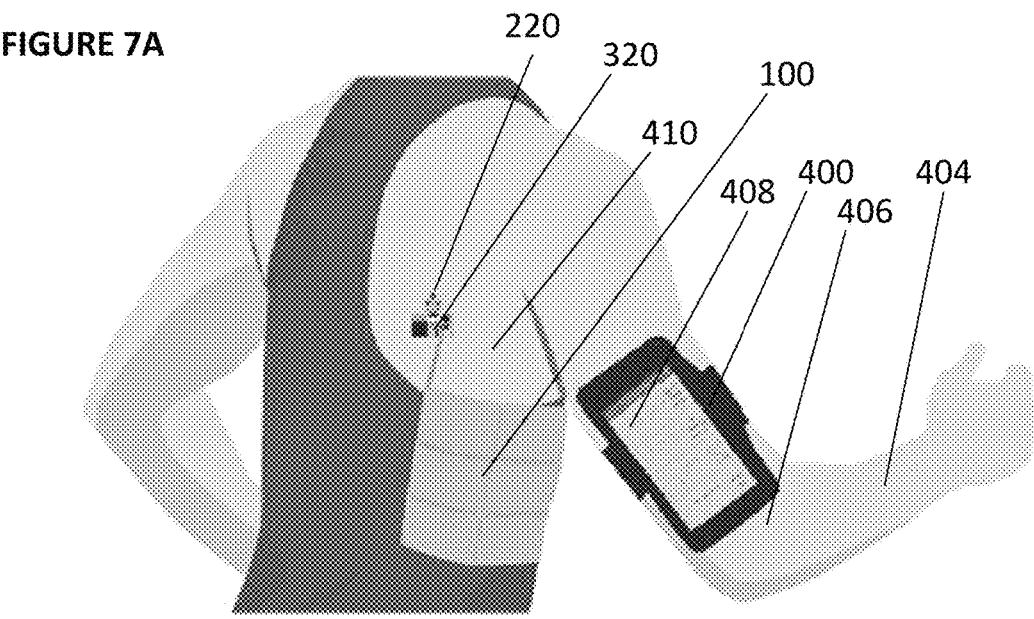
FIG. 7A is a diagram showing an example of a self-powered wearable biosensor system applied to a human body.

FIGS. 7A and 7B show how the self-powered wireless biosensor system may be worn on the body. FIG. 7A shows a 6-panel stator 100 attached to a human torso 410. The stator 100 is connected to circuitry 320 which includes power management modules and which is connected to the biosensor skin patch 220. A human subject may also wear an arm band 400 on an arm 404. On the outer side 406 of the arm, the arm band 400 may contain a user interface 408. The user interface 408 may be part of a mobile device. FIG. 7B shows the inner side 402 of the arm 404. The arm band 408 on the inner side 402 of the arm 404 may contain slider panels 120. When the human subject moves and/or exercises in a particular way, the slider panels 120 on the inner side 402 of the arm 404 slide against the stator panels 100 on the torso and power the entire system.

Figure 8:
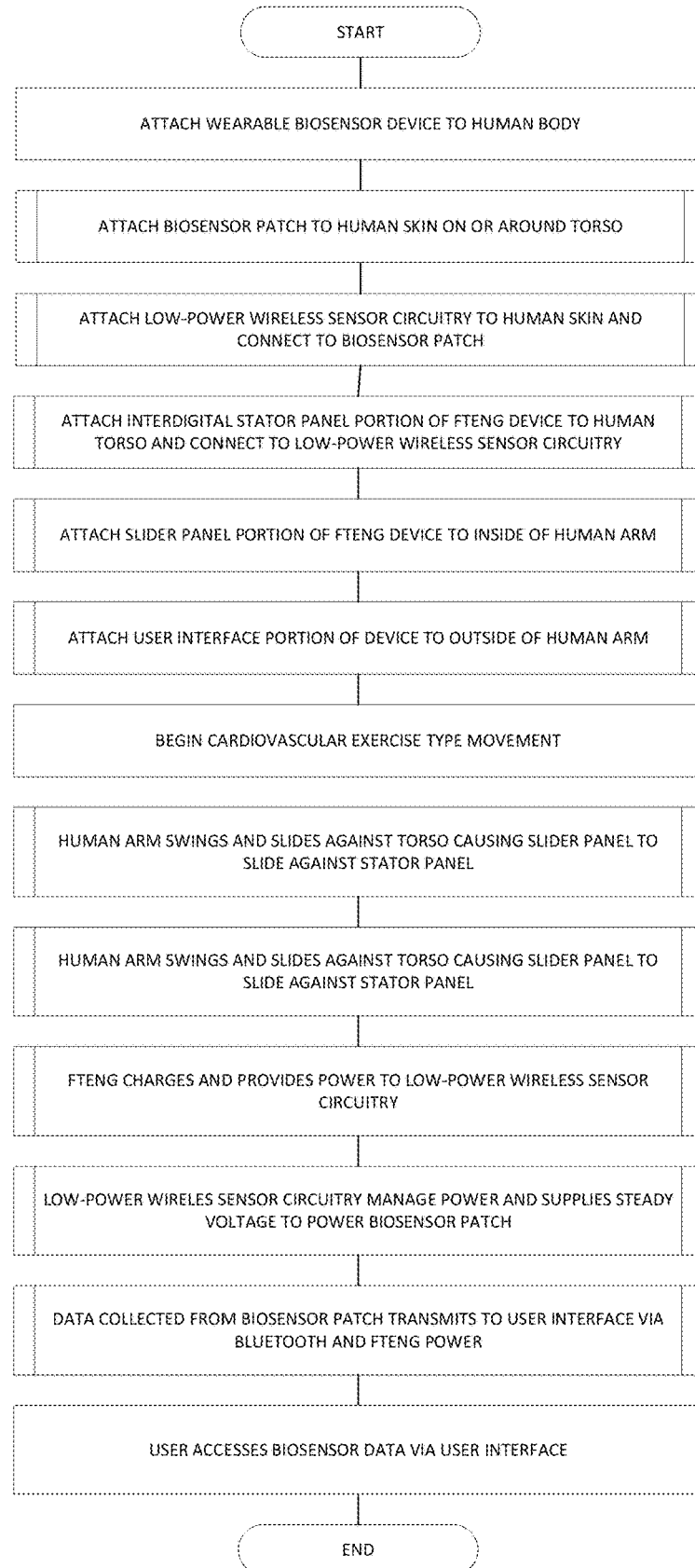
FIG. 8 is a flow diagram showing an example of a method for self-powering a wearable biosensor system.

FIG. 8 is a flow diagram showing an example of a method of powering a self-powered wearable biosensor system via human motion. The method may include first attaching a wearable biosensor to the human body. This may involve attaching a biosensor patch, such as a microfluidic sweat sensor patch to human skin on or near the torso area of the a human body. This may further involve attaching a low-power wireless sensor circuitry to the human skin and connecting the low-power wireless sensor circuitry to the sensor patch. This may further involve attaching an interdigital stator panel portion of an FTENG powering device to the human skin and connecting the stator to the low-power wireless sensor circuitry. This may also involve attaching a slider panel portion of an FTENG device to the inside of a human arm. This may also involve attaching a user interface portion of the system to the outside of a human arm.

A method of powering a self-powered wearable biosensor system may then involve beginning a cardiovascular exercise type of movement, such as running. During movement, the human arm may naturally swing and the inside portion of the human arm may slide against a torso area on the human body. This motion may cause the slider panel to slide across the stator panel. The sliding may charge the FTENG and provide power to the low-power wireless sensor circuitry. The low-power wireless sensor circuitry may manage the supplied power for efficient powering of the overall system and may supply a steady voltage. This steady voltage may power the biosensor patch and may enable transmission of data collected form the biosensor patch to a user interface. This transmission may be accomplished via Bluetooth or another wireless method. A user may then access biosensor data via the user interface.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A kinematic power system for a wearable device comprising:
   a stator comprising interdigital electrode arrays;
   a slider with multiple apertures configured in a grating pattern, wherein the slider slidably couples to the stator to enable movement between a first position relative to the stator and a second position relative to the stator;
   wherein the slider comprises a first triboelectric material deposited thereon and the stator comprises a second triboelectric material deposited thereon;
   wherein the kinematic power system is configured for use on a wearable device; and
   wherein the kinematic power system is configured to generate power from human motion.

2. The system of claim 1, wherein the second triboelectric material comprises polytetrafluoroethylene (PTFE).

3. The system of claim 1, wherein the first triboelectric material comprises copper.

4. The system of claim 1 wherein the interelectrode distance for the stator is between about 2 and about 18 millimeters.

5. The system of claim 1 wherein the apertures configured in a grating pattern each have a width dimension between about 1 and about 3 millimeters.

6. The system of claim 1 further comprising:
   a second stator comprising interdigital electrode arrays;
   a third stator comprising interdigital electrode arrays;
   a second slider with multiple apertures configured in a grating pattern; and
   a third slider with multiple apertures configured in a grating pattern.

7. The system of claim 6 further comprising:
   a fourth stator comprising interdigital electrode arrays;
   a fifth stator comprising interdigital electrode arrays; and
   a sixth stator comprising interdigital electrode arrays.

8. The system of claim 1 wherein the stator comprises a flexible printed circuit board technology (FPCB) fabricated stator.

9. A method for powering a wearable device comprising:
   wearing the wearable device, wherein the wearing comprises attaching the wearable device directly to human skin, the wearable device comprising:
   a stator panel comprising interdigital electrode arrays;
   a slider with multiple apertures configured in a grating pattern, wherein the slider slidably couples to the stator to enable movement between a first position relative to the stator and a second position relative to the stator; and
   moving, wherein the movement causes the slider to move between the first and second position on top of the stator.

10. The method of claim 9 wherein wearing the wearable device further comprises applying the stator panel to a human torso and applying the slider panel to the inside of a human arm.

11. The method of claim 9 wherein moving further comprises a type of exercise selected from the group consisting of: jogging, running, rowing, and training on an elliptical machine.

12. The method of claim 9 wherein moving comprises sustaining movement for a period of up to two hours.

13. The method of claim 9 further comprising accessing sample data collected by the wearable device using a user interface.

* * * * *